United States Patent
Disanza et al.

(10) Patent No.: US 9,669,179 B2
(45) Date of Patent: ***Jun. 6, 2017

(54) DEVICE FOR SECURING A BREATHING TUBE AND METHOD OF MANUFACTURING THE SAME

(71) Applicant: Airways Development LLC, Kenilworth, NJ (US)

(72) Inventors: Wayne W. Disanza, Toms River, NJ (US); Robert M. Landis, Mountainside, NJ (US)

(73) Assignee: Airways Development LLC, Kenilworth, NJ (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/679,186

(22) Filed: Apr. 6, 2015

(65) Prior Publication Data

US 2015/0209543 A1  Jul. 30, 2015

Related U.S. Application Data

(63) Continuation-in-part of application No. 13/688,492, filed on Nov. 29, 2012, now Pat. No. 9,095,672.
(Continued)

(51) Int. Cl.
*A61M 25/02* (2006.01)
*A61M 16/04* (2006.01)
(Continued)

(52) U.S. Cl.
CPC .... *A61M 16/0683* (2013.01); *A61M 16/0497* (2013.01); *A61M 16/0875* (2013.01);
(Continued)

(58) Field of Classification Search
CPC .. A41F 1/002; A42B 3/04; A42B 3/08; A44B 18/00; A44B 18/0049; A44B 18/0084;
(Continued)

(56) References Cited

U.S. PATENT DOCUMENTS 3,422,817 A   1/1969  Mishkin et al.
3,585,997 A   6/1971  Ancerewicz, Jr,
(Continued)

FOREIGN PATENT DOCUMENTS

EP   0145142 A1   6/1985

*Primary Examiner* — Annette Dixon
(74) *Attorney, Agent, or Firm* — Carter, DeLuca, Farrell & Schmidt, LLP

(57) ABSTRACT

A device for securing a tube includes a strip defining upper and lower surfaces and an attachment array on the lower surface thereof. First and second attachment members are coupled to the strip adjacent end portions thereof and define attachment arrays facing in the same direction as the upper surface of the strip. A third attachment member defines opposed surfaces having respective attachment arrays. A first of the attachment arrays is releasably engaged with the attachment array of the strip. The strip is configured to wrap around a tube with the attachment arrays of the attachment members and a second attachment array of the third attachment member releasably engaged with a strap member for securing the tube therebetween. The first and second attachment arrays of the third attachment member are configured such that the first attachment array defines a greater holding force than the second attachment array.

20 Claims, 1 Drawing Sheet

Related U.S. Application Data

(60) Provisional application No. 61/567,193, filed on Dec. 6, 2011.

(51) Int. Cl.
  *A61M 16/06* (2006.01)
  *A61M 16/08* (2006.01)
  *A44B 18/00* (2006.01)

(52) U.S. Cl.
  CPC ......... *A61M 25/02* (2013.01); *A44B 18/0084* (2013.01); *A61M 2025/026* (2013.01); *A61M 2025/0206* (2013.01); *A61M 2207/00* (2013.01); *A61M 2209/088* (2013.01); *A61M 2240/00* (2013.01); *Y10T 29/49826* (2015.01)

(58) Field of Classification Search
  CPC ........ A45C 13/1069; A45D 8/00; A45D 8/34; A45F 2005/104; A45F 2005/1073; A45F 3/00; A45F 3/02; A45F 3/14; A45F 5/00; A45F 5/10; A45F 5/1026; A61B 17/326; A61F 13/00021; A61F 13/00063; A61F 13/04; A61F 13/041; A61F 13/06; A61F 13/064; A61F 13/068; A61F 13/10; A61F 13/104; A61F 13/107; A61F 13/12; A61F 2013/00153; A61F 2013/00468; A61F 2013/00536; A61F 2013/00561; A61F 2013/00565; A61F 2013/00744; A61F 2013/00906; A61F 2013/0091; A61M 16/00; A61M 16/04; A61M 16/0447; A61M 16/0461; A61M 16/0488; A61M 16/0493; A61M 16/0497; A61M 16/06; A61M 16/0683; A61M 16/08; A61M 16/0875; A61M 2025/0206; A61M 2025/0213; A61M 2025/022; A61M 2025/0226; A61M 2025/024; A61M 2025/0253; A61M 2025/026; A61M 2025/0266; A61M 2025/0273; A61M 2209/06; A61M 2209/08; A61M 2209/088; A61M 2210/0618; A61M 2210/0625; A61M 2230/005; A61M 25/02
  USPC ............ 128/200.24, 200.26, 206.21, 206.27, 128/207.11, 207.13, 207.14, 207.15, 128/207.17, 207.18, DIG. 26; 604/174, 604/179, 180, 264, 304, 307, 308; 602/23, 48, 58, 61, 63, 901; 24/16 PB, 24/16 R, 17 A, 17 AP, 17 R, 20 EE, 20 R, 24/30.5 P, 30.5 R, 304, 306, 335, 339, 24/369, 370, 442, 446, 452, 67 AR, 24/DIG. 11; 294/141, 147, 149, 150, 294/164, 165, 170
  See application file for complete search history.

(56) References Cited

U.S. PATENT DOCUMENTS

| | | |
|---|---|---|
| 3,834,380 A | 9/1974 | Boyd |
| 3,878,849 A | 4/1975 | Muller et al. |
| 4,088,136 A | 5/1978 | Hasslinger et al. |
| 4,445,894 A | 5/1984 | Kovacs |
| 4,569,348 A | 2/1986 | Hasslinger |
| 4,571,245 A | 2/1986 | Hubbard et al. |
| 5,000,741 A | 3/1991 | Kalt |
| 5,038,778 A | 8/1991 | Lott |
| 5,058,579 A | 10/1991 | Terry et al. |
| 5,292,312 A | 3/1994 | Delk et al. |
| 5,411,484 A | 5/1995 | Shattuck |
| 5,692,268 A | 12/1997 | Case |
| 5,879,335 A | 3/1999 | Martinez et al. |
| 5,918,599 A | 7/1999 | Shesol |
| 2007/0235034 A1 | 10/2007 | Weaver |
| 2009/0126740 A1 | 5/2009 | Loescher |

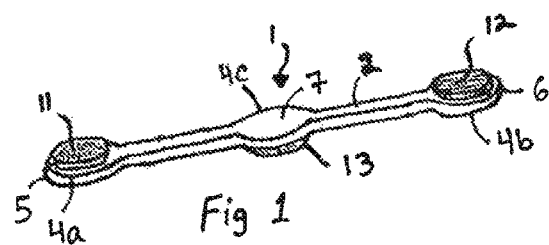
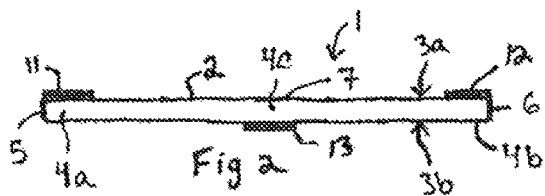
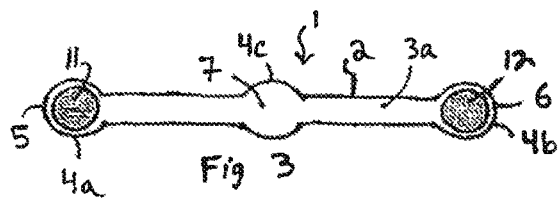
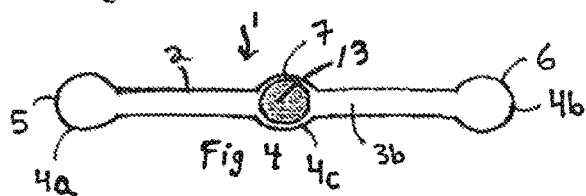
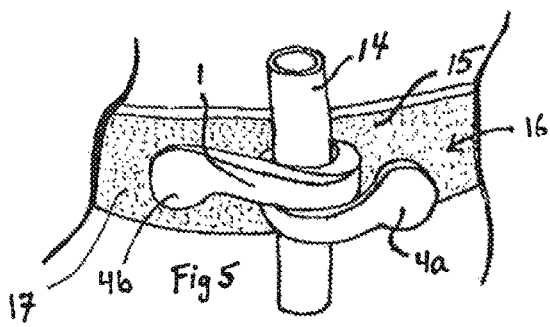
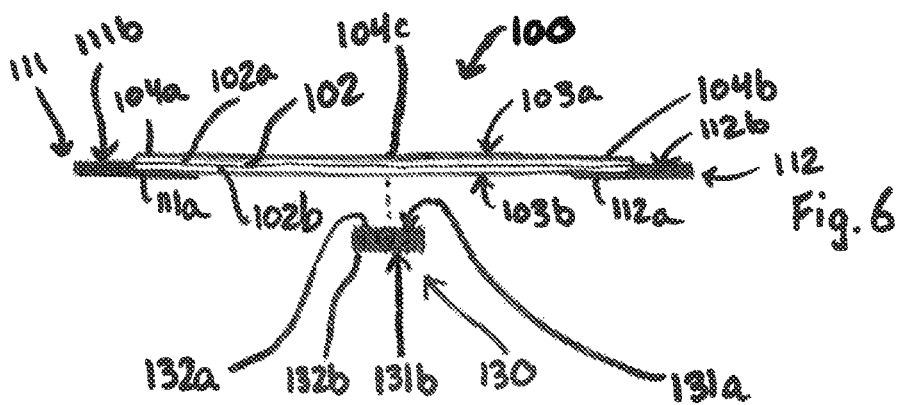

DEVICE FOR SECURING A BREATHING TUBE AND METHOD OF MANUFACTURING THE SAME

CROSS-REFERENCE TO RELATED APPLICATIONS

This application is a continuation-in-part application of U.S. patent application Ser. No. 13/688,492, filed on Nov. 29, 2012, now U.S. Pat. No. 9,095,672, which claims the benefit of, and priority to, U.S. Provisional Patent Application No. 61/567,193, filed on Dec. 6, 2011, the entire contents of each of which are hereby incorporated herein by reference.

BACKGROUND

Technical Field

The present disclosure relates to devices for securing tubes and, more particularly, to devices for securing a tube, e.g., a breathing tube, to a patient, e.g., to an infant's head, and methods of manufacturing the same.

Description of Related Art

Devices and methods of securing medical tubes to patients for receiving fluids and/or for the treatment of diseases are known. The most common method is the use of adhesive tape to secure tubing to the patient. However, more recent research has shown that removing adhesives from the skin of premature infants is the leading cause of infection in the intensive care unit. Thus, applying tape to a premature infant's skin is not desirable but, rather, a tapeless method is preferable. There are many known devices that utilize straps with hook/loop fasteners to secure tubing to a patient but none of these are designed with the premature infant's skin in mind. While the hazards of applying and removing adhesives from a premature infant's skin are known, there is a paucity of adhesive free options for the clinician at the bedside due at least in part to the design challenges associated with proper holding of life support tubes onto newborn infants and/or the ergonomic requirements thereof.

One area of particular interest is the securement of breathing tubes to a newborn infant's head. Typically, straps are wrapped around the infant's head such that the tube(s) can be attached to the straps. This "head gear" may also include a knit cap in combination with the straps. Once the "head gear" is fitted onto the infant's head, the supply tubes, e.g., breathing tubes, are attached to the "head gear." This method is preferred as it allows the tubes to move with the infant's head movements. While common practice, these devices and methods are tedious and laborious to manufacture and attach to an infant's head. In many cases clinicians are devising make shift methods using safety pins and rubber bands to stabilize breathing tubes. With the increasing costs of healthcare and an increasing burden on caregivers to treat more and more patients in a reduced amount of time, these tedious and laborious devices and methods are proving to be too time consuming. Accordingly, there is a need for a more effective, efficient, and ergonomic device for securing a tube to a patient, particularly with respect to the securement of a breathing tube to an infant's head. Further, there is a need for an effective and efficient manufacturing process for making such devices.

SUMMARY

In accordance with the present disclosure, a device for securing a tube in position is provided. The device includes a strip of material and first, second, and third attachment members. The strip of material defines a first surface and a second, opposed surface. The strip of material further includes a first end portion, a second end portion, and an intermediate portion. The first attachment member is disposed on the first surface of the strip of material and is positioned adjacent the first end portion. The second attachment member is disposed on the first surface of the strip of material and is positioned adjacent the second end portion. The third attachment member is disposed on the second surface of the strip of material and positioned is adjacent the intermediate portion. The strip of material is configured to wrap around a tube with the first, second, and third attachment members releasably engaging a strap member to secure a tube in position relative to the strap member.

In embodiments, the strip of material is formed from a foam and/or at least one of a stretchable, flexible, malleable, and elastomeric material.

In embodiments, the first surface of the strip of material defines a tacky anti-slip or sticky configuration to facilitate retention of the tube.

In embodiments, the first, second, and/or third attachment members include an array of hooks configured to releasably engage an array of loops.

In embodiments, the strip of material defines an expanded-dimension portion adjacent at least one of the first, second, and third attachment members.

A system for securing a tube in position provided in accordance with the present disclosure includes a strap member and a device. The strap member is configured to be secured to a patient and defines an outwardly-facing surface. The strap member includes an attachment structure disposed on the outwardly-facing surface. The device may include any or all of the features of the devices described above. The device is configured to wrap around a tube with the attachment structures of the first, second, and third attachment members releasably engaging the attachment structure of the strap member to secure tube in position relative to the strap member.

In embodiments, the strap member is formed from a non-stretchable or low stretch material suitable for wrapping around an infants head. Wrapping a new born infants head to tightly with elastic material is known to cause head molding.

In embodiments, the first, second, and third attachment members of the device each include an array of hooks and the attachment structure of the strap member includes an array of loops configured to releasably engage the arrays of hooks.

In embodiments, the tube is configured for positioning adjacent the intermediate portion of the strip of material with the first end portion wrapped about the tube in a first direction and the second end portion wrapped about the tube in a second direction.

In embodiments, the first attachment member is configured to engage the strap member on a first side of the tube and the second attachment member is configured to engage the strap member on a second, opposite side of the tube.

A method of securing a tube in position is also provided in accordance with the present disclosure. The method includes providing a strap member, providing a device (e.g., a device similar to any of the embodiments described above), attaching the strap member to a patient, engaging the intermediate portion of the device to the strap member, positioning a tube adjacent the first surface of the device at the intermediate portion thereof, wrapping the first end portion of the device about the tube in a first direction, engaging the first end portion of the device to the strap member, wrapping the second end portion of the device about the tube in a second direction, and engaging the second end portion of the device to the strap member.

In embodiments, engaging the intermediate portion of the device to the strap member includes engaging the third attachment member to the strap member, engaging the first end portion of the device to the strap member includes engaging the first attachment member to the strap member, and/or engaging the second end portion of the device to the strap member includes engaging the second attachment member to the strap member.

In embodiments, wrapping the first and second end portions about the tube in opposite directions provides 360 retention of the tube by the device.

In embodiments, attaching the strap member to a patient includes attaching the strap member about an infant's head Another device for securing a tube in position provided in accordance with the present disclosure includes a strip and first, second, and third attachment members. The strip defines an upper surface, a lower surface, a first end portion, a second end portion, and an intermediate portion. The intermediate portion of the strip on the lower surface thereof defines an attachment array. A first attachment member is coupled to the strip adjacent the first end portion thereof and defines an attachment array on a surface thereof. The attachment array of the first attachment member faces in the same direction as the upper surface of the strip. The second attachment member is coupled to the strip adjacent the second end portion thereof and defines an attachment array on a surface thereof. The attachment array of the second attachment member faces in the same direction as the upper surface of the strip. The third attachment member defines a first surface and a second surface. The first and second surfaces define respective first and second attachment arrays. The first attachment array is releasably engaged with the attachment array of the strip thereby releasably engaging the third attachment member with the lower surface of the strip adjacent the intermediate portion thereof. The strip is configured to wrap around a tube with the attachment arrays of the first and second attachment members and the second attachment array of the third attachment member releasably engaged with a strap member for securing the tube in position relative to the strap member. The first and second attachment arrays of the third attachment member are configured such that a holding force defined by the engagement of the first attachment array of the third attachment member with the attachment array of the strip is greater than a holding force defined by the engagement of the second attachment array of the third attachment member with the strap member.

In embodiments, the first and second attachment arrays of the third attachment member each define a plurality of hooks. The plurality of hooks of the first attachment array of the third attachment member may be more densely arranged as comparted to the plurality of hooks of the second attachment array of the third attachment member such that the holding force of the first attachment array is greater than the holding force of the second attachment array. Alternatively or additionally, at least one of materials, sizes, or orientations of the plurality of hooks of the first and second attachment arrays are selected such that the holding force of the first attachment array is greater than the holding force of the second attachment array.

In embodiments, the attachment array of the intermediate portion of the strip on the lower surface thereof defines a plurality of loops configured to releasably engage the plurality of hooks of the first attachment array of the third attachment member via a hook and loop engagement.

In embodiments, the first and second attachment members each include an adhering portion and an attachment portion. The adhering portions of the first and second attachment members are adhered to the lower surface of the strip while the attachment portions of the first and second attachment members overhang the respective first and second end portions of the strip.

In embodiments, the strip includes first and second materials adhered together such that the first material is positioned to define the upper surface and the second material is positioned to define the lower surface. The first material may be a foam material while the second material may be a loop fabric material.

Another system for securing a tube in position provided in accordance with the present disclosure includes a strap member and a device. The strap member is configured to be secured to a patient and defines an outwardly-facing surface defining an attachment array. The device may be configured similarly to any of the embodiments of the devices detailed above.

A method of manufacturing a device for securing a tube in position is also provided in accordance with the present disclosure. The method includes attaching a first attachment member to a first end portion of a strip defining an upper surface and a lower surface such that an attachment array of the first attachment member faces in the same direction as the upper surface of the strip. The strip includes an attachment array dispose on the lower surface thereof. The method further includes attaching a second attachment member to a second end portion of the strip such that an attachment array of the second attachment member faces in the same direction as the upper surface of the strip. Additionally, the method includes releasably engaging a first attachment array of a first surface of a third attachment member with the attachment array of the lower surface of the strip such that a second attachment array of a second surface of the third attachment member faces in the same direction as the lower surface of the strip. The first and second attachment arrays of the third attachment member are configured such that a holding force defined by the engagement of the first attachment array of the third attachment member with the attachment array of the strip is greater than a holding force defined by the engagement of the second attachment array of the third attachment member with a strap member to maintain the third attachment member in engagement with the strip through repeated engagement and disengagement of the second attachment array of the third attachment member with a strap member.

In embodiments, the method further includes forming the third attachment member by adhering a first material defining the first attachment array thereon with a second material defining the second attachment array thereon. At least one of materials, sizes, or orientations of the first and second attachment arrays are selected such that the holding force of the first attachment array is greater than the holding force of the second attachment array.

In embodiments, the first and second attachment members each include an adhering portion and an attachment portion. In such embodiments, the method further includes attaching the first attachment member by adhering the adhering portion of the first attachment member to the lower surface of the strip such that the attachment portion of the first attachment member overhangs the first end portion of the strip. The method additionally includes, in such embodiments, attaching the second attachment member by adhering the adhering portion of the second attachment member to the lower surface of the strip such that the attachment portion of the second attachment member overhangs the second end portion of the strip.

In embodiments, the method further includes forming the strip by adhering first and second strips of material together. The first strip of material may be formed from a foam and configured to define the upper surface of the strip. The second strip of material may be formed from a fabric material including the attachment array of the strip and may be configured to define the lower surface of the strip.

BRIEF DESCRIPTION OF THE DRAWINGS

The present disclosure is described herein with reference to the drawings wherein:

FIG. 1 is a perspective view of a tube securement device provided in accordance with the present disclosure;

FIG. 2 is a side view of the device of FIG. 1;

FIG. 3 is a top view of the device of FIG. 1;

FIG. 4 is a bottom view of the device of FIG. 1;

FIG. 5 is a perspective view of the device of FIG. 1 shown securing a tube in position; and FIG. 6 is a perspective view of another tube securement device provided in accordance with the present disclosure.

DETAILED DESCRIPTION

The present disclosure is described in detail with reference to the drawing figures wherein like reference numerals identify similar or identical elements.

Referring to FIGS. 1-5, a tube securement device provided in accordance with the present disclosure is shown generally identified by reference numeral 1. Device 1 is formed from a strip or length of material 2 having an upper surface 3a, a lower surface 3b, a first end portion 4a, a second end portion 4b, and an intermediate portion 4c. Length of material 2 may be formed from a foam, or other suitable stretchable, flexible, malleable, and/or elastomeric material. Further, length of material 2 may include a tacky anti-slip sticky, or adhesive outer surface to facilitate retention of a tube 14 therebetween (see FIG. 5). That is, length of material 2 may be formed from a tacky anti-slip sticky material, or may be coated with a tacky anti-slip sticky material. It is envisioned that length of material 2 define a length between about 1 and 4 inches and a thickness between about 0.125 inches and 0.25 inches, although other dimensions are also contemplated.

First, second, and third expanded-dimension portions 5, 6, 7, respectively, are defined along the length of material 2 at the first end portion 4a, second end portion 4b, and intermediate portion 4c, respectively, thereof. A first attachment member 11 is disposed on upper surface 3a of device 1 adjacent first expanded-dimension portion 5, a second attachment member 12 is disposed on upper surface 3a of device 1 adjacent second expanded-dimension portion 6, and a third attachment member 13 is disposed on lower surface 3b of device 1 adjacent third expanded-dimension portion 7. First, second, and third attachment members 11, 12, 13, respectively, and first, second, and third expanded-dimension portions 5, 6, 7, respectively, define generally circular or coin-shaped configurations, although other configurations are also contemplated. First, second, and third attachment members 11, 12, 13, respectively, may include any suitable attachment structure, e.g., an array of hooks, for releasably attaching members 11, 12, 13 to a complementary attachment structure, e.g., an array of loops.

With particular reference to FIG. 5, in conjunction with FIGS. 1-4, device 1 is configured for attachment to a strap 15 for securing a tube 14, e.g., a breathing tube, in position relative to a patient, e.g., on an infant's head. Strap 15 defines a generally flat configuration having a first surface 16. First surface 16 includes an attachment structure 17, e.g., an array of loops (or other suitable attachment structure configured to releasably engage attachment members 11, 12, 13), disposed thereon. Attachment structure 17 may substantially cover the entire surface 16, or may only cover portion(s) of surface 16.

In use, strap 15 is initially affixed to the patient. For example, with respect to securing a breathing tube to the head of an infant, strap 15 is secured about the infant's head. Strap 15 is oriented such that first surface 16 thereof is facing outwardly, e.g., away from the patient. Once strap 15 is positioned about the infant's head, device 1 is approximated relative to strap 15 with lower surface 3b of device 1 opposing first surface 16 of strap 15. Thus, upon further approximation and, ultimately, urging of device 1 into strap 15, the hooks (or other attachment structure) of attachment member 13 are engaged with the loops (or other feature) of attachment structure 17, thereby releasably engaging device 1 to strap 15 adjacent intermediate portion 4c. Due to the expanded-dimension portion 7, adjacent which attachment member 13 is disposed, a relatively greater surface area for engagement between the hooks and loops is provided, thus enabling a more secure engagement between device 1 and strap 15.

With attachment member 13 of device 1 secured to strap 15 as detailed above, tube 14 may be positioned adjacent the outwardly-facing upper surface 3a of device, at intermediate portion 4c of device 1. Next, first end portion 4a is bent, or wrapped over tube 14 in a first direction and second end portion 4b is bent, or wrapped over tube 14 in a second, opposite direction, to achieve the configuration shown in FIG. 5. First end portion 4a is then urged into engagement with strap 15 via the engagement of attachment member 11 with attachment structure 17. Likewise, second end portion 4b is then urged into engagement with strap 15 via the engagement of attachment member 12 with attachment structure 17. Similarly as described above, expanded-dimension portions 5 and 6 provide a greater surface area of engagement between first and second end portions 4a, 4b and strap 15, thus facilitating retention.

Once first and second end portions 4a, 4b are secured to strap 15 with tube 14 therebetween, as described above and as shown in FIG. 5, tube 14 is secured in position. In particular, device 1 provides 360 degree retention of tube 14 and further inhibits slippage of tube 14 due to the formation of device 1 from, or the coating of device 1 with, a sticky material. Thus, proper positioning of tube 14 is capable of being maintained, while facilitating attachment in an efficient, effective, and ergonomic manner.

Referring to FIG. 6, another tube securement device provided in accordance with the present disclosure is shown generally identified by reference numeral 100. Device 100 is similar to device 1 (FIGS. 1-5) and may include any of the features thereof, and vice versa. For purposes of brevity, only the differences between device 100 and device 1 (FIGS. 1-5) will be detailed below while similarities will be summarily described or omitted entirely.

Device 100 includes a strip 102 having an upper surface 103a, a lower surface 103b, a first end portion 104a, a second end portion 104b, and an intermediate portion 104c. Strip 102 is formed via adhering a foam material 102a to a loop fabric material 102b, e.g., a fabric including an array of loops capable of engaging an array of hooks via a hook and loop fastening engagement, such that foam material 102a is exposed on upper surface 103a of strip 102 and the array of loops of loop fabric material 102b are exposed on lower surface 103b of strip 102.

First and second attachment members 111, 112 may be disposed on upper surface 103a of strip 102, similarly as detailed above. Alternatively, as shown in FIG. 6, first and second attachment members 111, 112 may each include an adhering portion 111a, 112a that is adhered to lower surface 103b, as shown in FIG. 6, and an attachment portion that overhangs strip 102 and defines an attachment surface 111b, 112b facing in the same direction as upper surface 103a. Attachment surfaces 111b, 112b each include an array of hooks capable of engaging an array of loops, e.g., those of loop fabric material 102b, via a hook and loop fastening engagement.

A third attachment member 130 is releasably engaged with lower surface 103b of strip 102 on intermediate portion 104c thereof. Third attachment member 130 includes first and second surfaces 131a, 131b and may be formed via adhering first and second hook fabric materials to one another such that first and second surfaces 131a, 131b of the respective first and second hook fabric materials are exposed on either side of third attachment member 130. More specifically, first surface 131a of first hook fabric material includes an array of hooks 132a disposed thereon and second surface 131b of second hook fabric material includes an array of hooks 132b disposed therein. First array of hooks 132a is configured to releasably engage loop fabric material 102b of strip 102, while second array of hooks 132b is configured to releasably engage a strap 15 for securing a tube 14, e.g., a breathing tube, in position relative to a patient, similarly as detailed above (see FIG. 5). First array of hooks 132a is configured to define a greater engagement or holding force as compared to second array of hooks 132b. This may be accomplished by varying the density of the hooks, the material forming the hooks, the size of the hooks, and/or the orientation of the hooks on first array 132a as compared to second array 132b. Other suitable configurations for the arrays of hooks 132a, 132b to define different holding forces may additionally or alternatively be provided.

During manufacturing, third attachment member 130 is engaged with strip 102 on intermediate portion 104c thereof via engagement of first array of hooks 132a of first surface 131a of third attachment member 130 with loop fabric material 102b of lower surface 103b of strip 102. Despite this engagement being releasable, third attachment member 130 remains engaged with strip 102 throughout repeated use of device 100, e.g., repeated engagement and disengagement of second array of hooks 132b of third attachment member 130 with strap 15 (FIG. 5), due to the greater holding force of first array 132a as compared to second array 132b.

The above-detailed configuration of device 100 is advantageous in that it allows for more efficient manufacturing by obviating the need to adhere or otherwise permanently engage third attachment member 130 to intermediate portion 104c of strip 102. In particular, the above-detailed configuration of device 100 facilitates the manufacture thereof as compared to a device where first and second attachment members are adhered to a first side of a strip (or oriented in a first direction) while a third attachment member is adhered to a second, opposite side of the strip (or oriented in a second, opposite direction).

From the foregoing and with reference to the various figure drawings, those skilled in the art will appreciate that certain modifications can also be made to the present disclosure without departing from the scope of the same. It is not intended that the above description be limiting but, rather, that the above description be construed merely as an exemplification of the present disclosure. Those skilled in the art will envision other modifications within the scope and spirit of the claims appended hereto.

What is claimed is:

1. A device for securing a tube in position, comprising:
   a strip defining an upper surface and a lower surface, the strip including a first end portion, a second end portion, and an intermediate portion, the intermediate portion of the strip on the lower surface thereof defining an attachment array;
   a first attachment member coupled to the strip adjacent the first end portion thereof and defining an attachment array on a surface thereof, the attachment array of the first attachment member facing in the same direction as the upper surface of the strip;
   a second attachment member coupled to the strip adjacent the second end portion thereof and defining an attachment array on a surface thereof, the attachment array of the second attachment member facing in the same direction as the upper surface of the strip; and
   a third attachment member defining a first surface and a second surface, the first and second surfaces defining respective first and second attachment arrays, the first attachment array releasably engaged with the attachment array of the strip thereby releasably engaging the third attachment member with the lower surface of the strip adjacent the intermediate portion thereof,
   wherein the strip is configured to wrap around a tube with the attachment arrays of the first and second attachment members and the second attachment array of the third attachment member releasably engaged with a strap member for securing the tube in position relative to the strap member, and
   wherein the first and second attachment arrays of the third attachment member are configured such that a holding force defined by the engagement of the first attachment array of the third attachment member with the attachment array of the strip is greater than a holding force defined by the engagement of the second attachment array of the third attachment member with the strap member.

2. The device according to claim 1, wherein the first and second attachment arrays of the third attachment member each define a plurality of hooks.

3. The device according to claim 2, wherein the plurality of hooks of the first attachment array of the third attachment member are more densely arranged as comparted to the plurality of hooks of the second attachment array of the third attachment member such that the holding force of the first attachment array is greater than the holding force of the second attachment array.

4. The device according to claim 2, wherein at least one of materials, sizes, or orientations of the plurality of hooks of the first and second attachment arrays are selected such that the holding force of the first attachment array is greater than the holding force of the second attachment array.

5. The device according to claim 2, wherein the attachment array of the intermediate portion of the strip on the lower surface thereof defines a plurality of loops configured to releasably engage the plurality of hooks of the first attachment array of the third attachment member via a hook and loop engagement.

6. The device according to claim 1, wherein the first and second attachment members each include an adhering portion and an attachment portion, the adhering portions of the first and second attachment members adhered to the lower surface of the strip, the attachment portions of the first and second attachment members overhanging the respective first and second end portions of the strip.

7. The device according to claim 1, wherein the strip includes first and second materials adhered together, the first material positioned to define the upper surface and the second material positioned to define the lower surface.

8. The device according to claim 7, wherein the first material is a foam material and the second material is a loop fabric material.

9. A system for securing a tube in position, comprising:
a strap member configured to be secured to a patient, the strap member defining an outwardly-facing surface defining an attachment array; and
a device, including:
a strip defining an upper surface and a lower surface, the strip including a first end portion, a second end portion, and an intermediate portion, the intermediate portion of the strip on the lower surface thereof defining an attachment array;
a first attachment member coupled to the strip adjacent the first end portion thereof and defining an attachment array on a surface thereof, the attachment array of the first attachment member facing in the same direction as the upper surface of the strip;
a second attachment member coupled to the strip adjacent the second end portion thereof and defining an attachment array on a surface thereof, the attachment array of the second attachment member facing in the same direction as the upper surface of the strip; and
a third attachment member defining a first surface and a second surface, the first and second surfaces defining respective first and second attachment arrays, the first attachment array releasably engaged with the attachment array of the strip thereby releasably engaging the third attachment member with the lower surface of the strip adjacent the intermediate portion thereof,
wherein the strip is configured to wrap around a tube with the attachment arrays of the first and second attachment members and the second attachment array of the third attachment member releasably engaged with the attachment array of the strap member for securing the tube in position relative to the strap member, and
wherein the first and second attachment arrays of the third attachment member are configured such that a holding force defined by the engagement of the first attachment array of the third attachment member with the attachment array of the strip is greater than a holding force defined by the engagement of the second attachment array of the third attachment member with the attachment array of the strap member.

10. The system according to claim 9, wherein the first and second attachment arrays of the third attachment member each define a plurality of hooks.

11. The system according to claim 10, wherein the plurality of hooks of the first attachment array of the third attachment member are more densely arranged as comparted to the plurality of hooks of the second attachment array of the third attachment member such that the holding force of the first attachment array is greater than the holding force of the second attachment array.

12. The system according to claim 10, wherein at least one of materials, sizes, or orientations of the plurality of hooks of the first and second attachment arrays are selected such that the holding force of the first attachment array is greater than the holding force of the second attachment array.

13. The system according to claim 9, wherein the attachment array of the intermediate portion of the strip on the lower surface thereof defines a plurality of loops configured to releasably engage the plurality of hooks of the first attachment array of the third attachment member via a hook and loop engagement, and wherein the attachment array of the outwardly-facing surface of the strap member defines a plurality of loops configured to releasably engage the plurality of hooks of the second attachment array of the third attachment member via a hook and loop engagement.

14. The system according to claim 9, wherein the first and second attachment members each include an adhering portion and an attachment portion, the adhering portions of the first and second attachment members adhered to the lower surface of the strip, the attachment portions of the first and second attachment members overhanging the respective first and second end portions of the strip.

15. The system according to claim 9, wherein the strip includes first and second materials adhered together, the first material positioned to define the upper surface and the second material positioned to define the lower surface.

16. The system according to claim 15, wherein the first material is a foam material and the second material is a loop fabric material.

17. A method of manufacturing a device for securing a tube in position, the method comprising:
attaching a first attachment member to a first end portion of a strip defining an upper surface and a lower surface such that an attachment array of the first attachment member faces in the same direction as the upper surface of the strip, wherein the strip includes an attachment array dispose on the lower surface thereof;
attaching a second attachment member to a second end portion of the strip such that an attachment array of the second attachment member faces in the same direction as the upper surface of the strip; and
releasably engaging a first attachment array of a first surface of a third attachment member with the attachment array of the lower surface of the strip such that a second attachment array of a second surface of the third attachment member faces in the same direction as the lower surface of the strip, wherein the first and second attachment arrays of the third attachment member are configured such that a holding force defined by the engagement of the first attachment array of the third attachment member with the attachment array of the strip is greater than a holding force defined by the engagement of the second attachment array of the third attachment member with a strap member to maintain the third attachment member in engagement with the strip through repeated engagement and disengagement of the second attachment array of the third attachment member with a strap member.

18. The method according to claim 17, further including forming the third attachment member by adhering a first material defining the first attachment array thereon with a second material defining the second attachment array thereon, wherein at least one of materials, sizes, or orientations of the first and second attachment arrays are selected such that the holding force of the first attachment array is greater than the holding force of the second attachment array.

19. The method according to claim 17, wherein the first and second attachment members each include an adhering portion and an attachment portion, and wherein:
- attaching the first attachment member includes adhering the adhering portion of the first attachment member to the lower surface of the strip such that the attachment portion of the first attachment member overhangs the first end portion of the strip; and
- attaching the second attachment member includes adhering the adhering portion of the second attachment member to the lower surface of the strip such that the attachment portion of the second attachment member overhangs the second end portion of the strip.

20. The method according to claim 17, further including forming the strip by adhering first and second strips of material together, the first strip of material formed from a foam and defining the upper surface of the strip and the second strip of material formed from a fabric material defining the attachment array of the strip and the lower surface of the strip.

\* \* \* \* \*